(12) United States Patent
Venkatesan et al.

(10) Patent No.: US 9,427,137 B2
(45) Date of Patent: Aug. 30, 2016

(54) IMAGING A PATIENT'S INTERIOR

(71) Applicant: KONINKLIJKE PHILIPS N.V., Eindhoven (NL)

(72) Inventors: Shankar Mosur Venkatesan, Bangalore (IN); Pallavi Vajinepalli, Bangalore (IN); Vipin Gupta, Bangalore (IN); Sushanth Govinahallisathyanarayana, Bangalore (IN); Mandar Shirikant Kulkarni, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/891,147

(22) PCT Filed: May 15, 2014

(86) PCT No.: PCT/EP2014/059901
§ 371 (c)(1),
(2) Date: Nov. 13, 2015

(87) PCT Pub. No.: WO2014/184274
PCT Pub. Date: Nov. 20, 2014

(65) Prior Publication Data
US 2016/0073853 A1  Mar. 17, 2016

(30) Foreign Application Priority Data
May 15, 2013  (EP) .................................. 13167853

(51) Int. Cl.
| | |
|---|---|
| *H04N 1/04* | (2006.01) |
| *A61B 1/00* | (2006.01) |
| *G06T 7/00* | (2006.01) |
| *A61B 1/06* | (2006.01) |
| *A61B 1/04* | (2006.01) |
| *A61B 1/303* | (2006.01) |
| *A61B 1/313* | (2006.01) |
| *A61B 3/12* | (2006.01) |
| *H04N 5/225* | (2006.01) |
| *H04N 7/18* | (2006.01) |

(52) U.S. Cl.
CPC ............. *A61B 1/00006* (2013.01); *A61B 1/04* (2013.01); *A61B 1/0607* (2013.01);
(Continued)

(58) Field of Classification Search
IPC ........................................................ A61B 1/00
See application file for complete search history.

(56) References Cited

U.S. PATENT DOCUMENTS

| | | | | |
|---|---|---|---|---|
| 5,150,336 A | * | 9/1992 | Sullivan | G01S 13/42 367/103 |
| 5,708,498 A | * | 1/1998 | Rioux | G01B 11/24 356/326 |

(Continued)

FOREIGN PATENT DOCUMENTS

| | | |
|---|---|---|
| DE | 19532095 C1 | 8/1996 |
| DE | 102010009884 A1 | 9/2011 |

(Continued)

OTHER PUBLICATIONS

Woodham, R.J. "Photometric Method for Determining Surface Orientation from Multiple Images", Optical Engineering, 1980, vol. 19, No. 1, pp. 139-144.

*Primary Examiner* — Tracy Li

(57) ABSTRACT

A system (100) is provided for imaging a patient's interior. The system comprises an imaging sensor (120) for acquiring a series of images of a region of interest (020) in the patient's interior, and a plurality of light sources (140) for illuminating the region of interest in the patient's interior from different light source directions (152-156). A light controller (160) is provided for controlling individual ones (142-146) of the plurality of light sources (140) to dynamically vary the light source directions (152-156) during said acquiring. Moreover, a processor (180) is provided for obtaining lighting data (164) indicative of the dynamically varying light source directions. The processor (180) is further arranged for using the lighting data to apply a photometric stereo technique to the image data so as to establish a three-dimensional [3D] surface profile of the region of interest. The processor (180) is further provided to detect insufficiently illuminated areas of the region of interest (020-024) in the images acquired by the imaging sensor (120), using the 3D surface profile of the region of interest. Accordingly, the system is enabled to establish a 3D surface profile of the region of interest from a series of images in a convenient and cost-effective manner.

14 Claims, 4 Drawing Sheets

(52) U.S. Cl.
CPC ............ *A61B 1/0661* (2013.01); *A61B 1/303* (2013.01); *A61B 1/3132* (2013.01); *A61B 3/12* (2013.01); *G06T 7/0073* (2013.01); *H04N 5/2256* (2013.01); *H04N 7/183* (2013.01); *G06T 2207/10021* (2013.01); *G06T 2207/10068* (2013.01); *G06T 2207/10152* (2013.01); *G06T 2207/30004* (2013.01); *H04N 2005/2255* (2013.01)

(56) References Cited

U.S. PATENT DOCUMENTS

| | | | |
|---|---|---|---|
| 6,733,458 B1 * | 5/2004 | Steins | A61B 8/0833 600/461 |
| 7,652,772 B2 | 1/2010 | Backman | |
| 2002/0103439 A1 * | 8/2002 | Zeng | G01J 3/0289 600/476 |
| 2005/0254720 A1 | 11/2005 | Tan | |
| 2005/0288588 A1 * | 12/2005 | Weber | A61B 8/483 600/447 |
| 2010/0026785 A1 | 2/2010 | Soto-Thompson | |
| 2010/0141780 A1 * | 6/2010 | Tan | H04N 9/3182 348/222.1 |
| 2010/0149315 A1 | 6/2010 | Qu | |
| 2011/0210261 A1 * | 9/2011 | Maurer, Jr. | A61N 5/10 250/393 |

FOREIGN PATENT DOCUMENTS

| | | |
|---|---|---|
| EP | 1326432 A2 | 7/2003 |
| WO | 2009000078 A1 | 12/2008 |
| WO | 2011146007 A1 | 11/2011 |
| WO | 2012123881 A2 | 9/2012 |
| WO | 2014006549 A1 | 1/2014 |

* cited by examiner

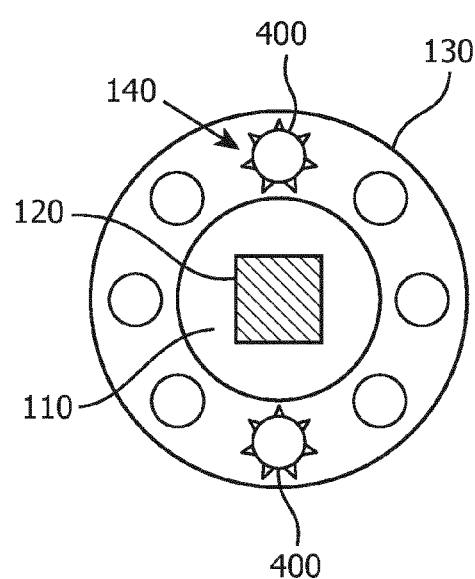
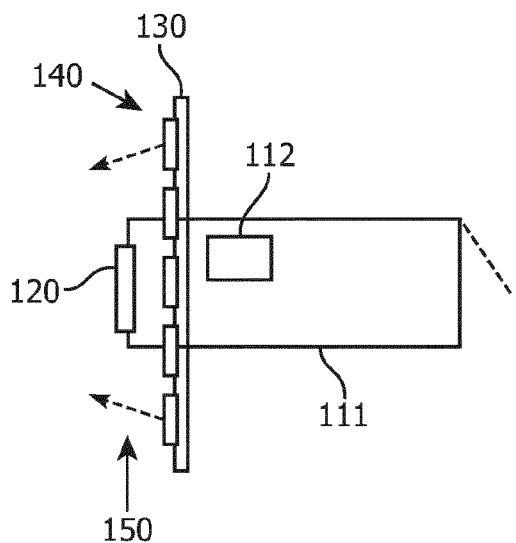
FIG. 4a    FIG. 4b
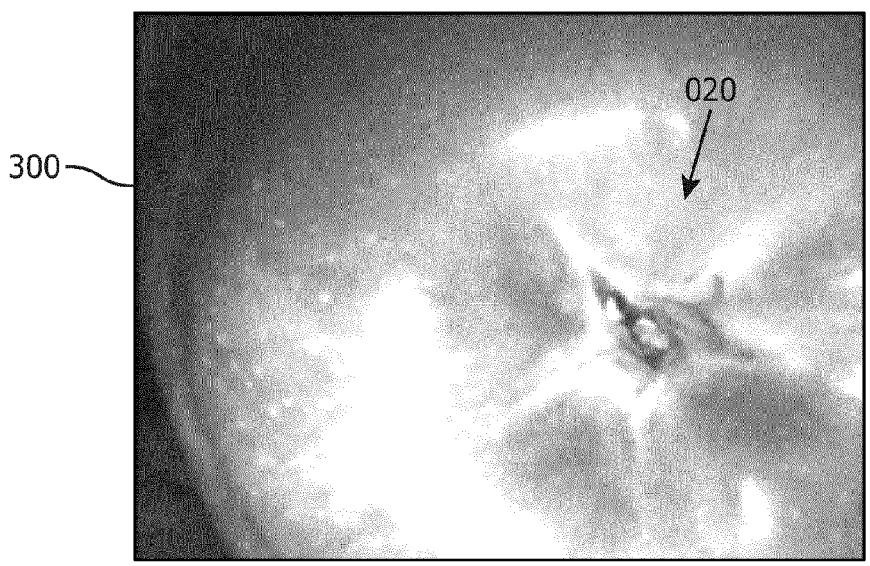
FIG. 5

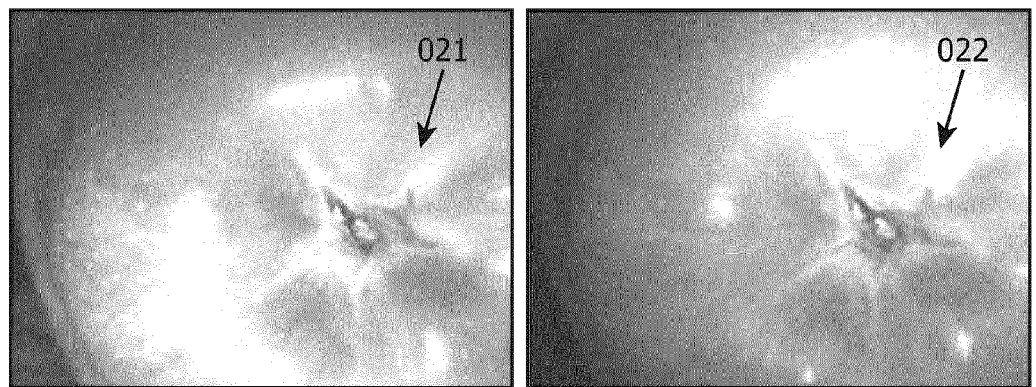
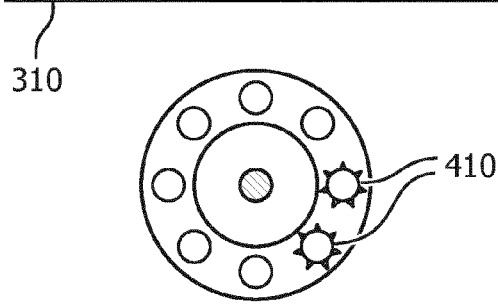
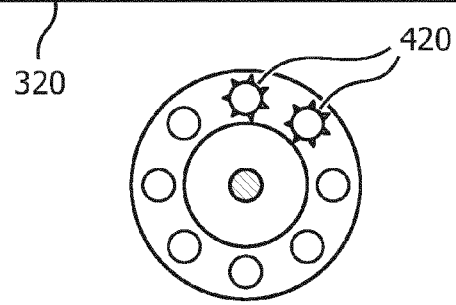
FIG. 6a  FIG. 6b
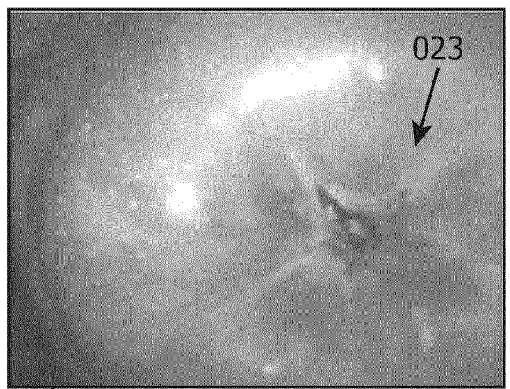
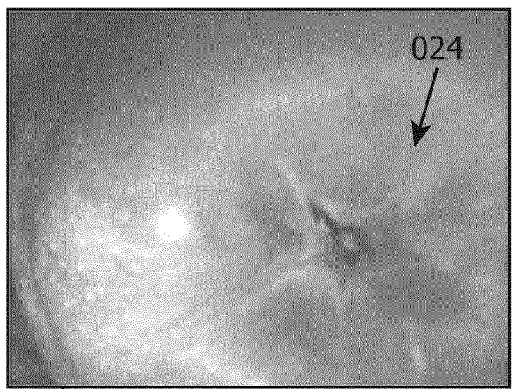
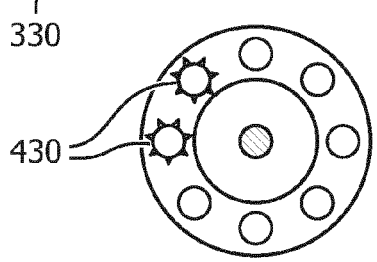
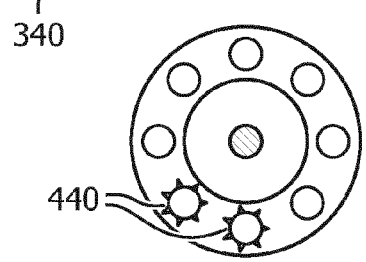
FIG. 6c  FIG. 6d

IMAGING A PATIENT'S INTERIOR

CROSS-REFERENCE TO PRIOR APPLICATIONS

This application is the U.S. National Phase application under 35 U.S.C. §371 of International Application No. PCT/EP2014/059901, filed on May 15, 2014, which claims the benefit of U.S. Provisional Patent Application No. or European Patent Application No. 13167853.4, filed on May 15, 2013. These applications are hereby incorporated by reference herein.

FIELD OF THE INVENTION

The invention relates to a system and a method for imaging a patient's interior and a computer program product for causing a processor system to perform the method.

Medical diagnosis frequently involves imaging of a patient's interior. For example, in the detection of cervical cancer, a clinician may examine a patient's cervix using a colposcope, i.e., a device which allows the clinician to grade precancerous and early invasive cervical cancer lesions and to identify locations to perform biopsies. A colposcope typically comprises an imaging sensor to acquire one or more images of a region of interest in the patient's interior, e.g., the cervix or part thereof. Moreover, such a colposcope typically comprises a light source to illuminate the region of interest while acquiring the images. As a result, the clinician is provided with images of the region of interest being illuminated.

BACKGROUND OF THE INVENTION

It is desirable to establish a three-dimensional [3D] surface profile of a region of interest shown in such images, e.g., to enable 3D motion tracking of the region of interest.

US 2010/0149315 A1 describes an imaging system and method for colposcopic imaging in which three-dimensional (3D) imaging information is combined with motion tracking information. The system includes at least one structured light source for projecting a structured light pattern on the portion of an object and at least one camera for imaging the portion of the object and the structured light pattern. It is said that the structured light source projects the structured light pattern onto the imaged object for generating feature points, measures the feature points, and uses them for reconstructing the 3D surface topology of the imaged object. It is further said that the structured light sources may include a laser light source for generating a laser beam, a holographic grating for diffracting the laser beam, and one or more reflective surfaces for directing the diffracted laser beam.

A problem of the imaging system of US 2010/0149315 A1 is that it is complex as it requires the use of different types of light sources during the colposcopic imaging to enable reconstructing the 3D surface topology of the imaged object.

DE102010009884 A1 discloses an endoscope inserted into the body cavity, wherein a region of the inner surface is illuminated from different directions, one after another in time, by means of at least three light sources. The light sources are spaced apart from each other on or in the endoscope. Using a camera one image is recorded in respect of each of the illuminated region from the same camera position, so that, for a plurality of object points of the region, said associated image points comprise the same image coordinates for each of said object points in each of the three images, one after another in time. Information about the three-dimensional structure of the region is derived from the intensities of the image points in each of the images.

US2005/0254720 A1 describes a method to enhance an output image of a 3D object. A set of input images are acquired of a 3D object. Each one of the input images is illuminated by a different one of a set of lights placed at different positions with respect to the 3D object. Boundaries of shadows are detected in the set of input images by comparing the set of input images. The boundaries of shadows that are closer to a direction of the set of lights are marked as depth edge pixels.

DE19532095 C1 discloses an endoscope having a tube with a lens set into the tip that focuses the image of the observed object into a fibre optic conductor that has a further lens directing the image onto a video camera. The tip section has lighting output groups positioned on opposite sides and at the ends of conductors. The image is obtained with alternating lighting from the two groups and this creates a recorded image having a stereoscopic effect.

In-vivo images including three-dimensional or surface orientation information may be captured and viewed. EP1326432 A2 describes an in-vivo site being illuminated by a plurality of sources, and the resulting reflected images may be used to provide three-dimensional or surface orientation information on the in-vivo site. The system may include a swallowable capsule.

The above referred prior arts do not refer to illuminating the region of interest together with identifying the insufficiently illuminated region and providing a solution to overcome the insufficient illumination of the region of interest.

SUMMARY OF THE INVENTION

It would be advantageous to have a less complex system or method for establishing a 3D surface profile of a region of interest in a patient's interior.

To better address this concern, a first aspect of the invention provides a system for imaging a patient's interior, the system comprising an imaging sensor for acquiring, in the form of image data, a series of images of a region of interest in the patient's interior, the system further comprising:
  a plurality of light sources for illuminating the region of interest in the patient's interior from different light source directions:
  a light controller for controlling individual ones of the plurality of light sources to illuminate the region of interest with different subsets of the plurality of light sources when acquiring the series of images, thereby establishing dynamically varying light source directions during said acquiring; and
  a processor for i) obtaining lighting data indicative of the dynamically varying light source directions, ii) using the lighting data to apply a photometric stereo technique to the image data for estimating a plurality of surface parameters defining a surface of the region of interest in the series of images, iii) based on the surface parameters, establishing a three-dimensional [3D] surface profile of the region of interest, and iv) detecting insufficiently illuminated areas of the region of interest in the images acquired by the imaging sensor, using the 3D surface profile of the region of interest.

In a further aspect of the invention, a workstation and an imaging apparatus is provided comprising the light controller and the processor of system set forth.

In a further aspect of the invention, a method is provided for imaging a patient's interior, the method comprising acquiring, in the form of image data, a series of images of a region of interest in the patient's interior, the region of interest being illuminated in the patient's interior by a plurality of light sources from different light source directions, the method further comprising:

controlling individual ones of the plurality of light sources to illuminate the region of interest with different subsets of the plurality of light sources when acquiring the series of images, thereby establishing dynamically varying light source directions during said acquiring;

obtaining lighting data indicative of the dynamic sequence of light source directions;

using the lighting data to apply a photometric stereo technique to the image data for estimating a plurality of surface parameters defining a surface of the region of interest in the series of images;

based on the surface parameters, establishing a three-dimensional [3D] surface profile of the region of interest; and detecting insufficiently illuminated areas of the region of interest in the images acquired by the imaging sensor, using the 3D surface profile of the region of interest.

In a further aspect of the invention, a computer program product is provided comprising instructions for causing a processor system to perform the method set forth.

The above measures provide a system and a method which make use of an imaging sensor to acquire a series of images of a region of interest in the patient's interior. The series of images shows the region of interest at different moments in time. For example, the series of images may be constituted by a video sequence showing the region of interest at consecutive moments in time. Here, the term region of interest refers to a portion of the patient's interior which is shown in the series of images. Said region is a region of interest since it is a subject of the imaging and thus indicates interest from a user of the system.

A plurality of light sources are provided which are suitable for illuminating the region of interest in the patient's interior, e.g., by being arranged nearby or inside an opening to the patient's interior. As the region of interest is illuminated in the patient's interior, the region of interest is made visible or better visible in the series of images.

Each individual light source is differently positioned with respect to the region of interest, thereby enabling the plurality of light sources to illuminate the region of interest from different light source directions. Additionally, a light controller is provided which controls each of the plurality of light sources individually. As a result, the light controller can effect an illumination of the region of interest with a subset of individual light sources, i.e., a specific selection amongst the plurality of light sources. The region of interest can therefore, when being illuminated by a given subset of light sources, not, or substantially not, be illuminated by others of the plurality of light sources which are not included in said subset.

The light controller is arranged for controlling the plurality of light sources such that the region of interest is illuminated with different subsets of the plurality of light sources when acquiring the series of images. Accordingly, the series of images is at least in part comprised of images in which the region of interest is differently illuminated, namely from different light source directions, given that different subsets from the plurality of light sources are used. For example, the region of interest may be illuminated in a first image from a first set of light source directions provided by a first subset of the plurality of light sources, and in another image from another set of light source directions provided by another subset of the plurality of light sources. Accordingly, the light source directions from which the region of interest is illuminated dynamically vary over at least part of the series of images. It is noted here that the different subsets of the plurality of light sources may include one or more of the same, i.e., overlapping, light sources and thus may provide overlapping light source directions. Nevertheless, the different subsets are different in that they differ by at least one light source, thereby providing at least one non-overlapping light source direction.

A processor is provided which obtains lighting data which is indicative of the dynamically varying light source directions that were used during the acquiring of the series of images. For example, the lighting data may be comprised of data which lists the light source directions used in the illumination of the region of interest for each of the series of images. Another example is that the lighting data may be comprised in part of dynamic data obtained from the lighting controller which indicates which different subsets were used in the illumination of the region of interest in each of the series of images, and in part of static data which indicates the light source directions provided by each of the different subsets of the plurality of light sources. The processor uses the lighting data together with the image data in a photometric stereo technique. Such techniques are known in the fields of optical engineering and image processing, e.g., from a paper "Photometric method for determining surface orientation from multiple images", Woodham R. J., Optical Engineering, January/February 1980, Vol. 19, No. 1, pp. 139-144, with said techniques enabling surface parameters to be estimated which define a surface of an object, e.g. surface normals or other surface orientation parameters, based on the object being illuminated from varying illumination directions in successive images. The processor applies such a photometric stereo technique to the series of images to estimate a plurality of surface parameters which define a surface of the region of interest in the series of images. Furthermore, the processor uses the surface parameters to establish a 3D surface profile of the region of interest, e.g., by presenting the surface parameters in accordance with a position on the surface of the region of interest.

The above measures provide a combination of light sources, light source control and processing which enable a series of images of a region of interest to be acquired from which a 3D surface profile of the region of interest is subsequently established. By providing, instead of a single light source, a plurality of different light sources and by providing a light controller which is arranged for individually controlling said light sources, the region of interest in the patient's interior can be illuminated from different light source directions. By the light controller effecting the dynamically varying light source directions during the acquiring of the series of images and the processor obtaining lighting data indicative of the dynamically varying light source directions, the processor is enabled to estimate the plurality of surface parameters defining the surface of the region of interest in the series of images, namely by making use of the photometric stereo technique. Accordingly, the system can establish the 3D surface profile of the region of interest from the series of images. It is therefore not needed to provide additional light sources specifically for establishing the 3D surface profile of the region of interest. Rather, a plurality of light sources are provided which serve for normally illuminating the region of interest, yet which, when being controlled by the light controller, provide the dynamically varying light source directions which enable acquiring a series of images suitable for the photometric stereo technique. The inventors have recognized that although such a photometric stereo technique is bound to limitations, e.g., since shadows cannot be accounted for properly, the technique is well suited for the imaging of the patient's interior using the above system since surfaces such as the cervical region are typically convex, there are no tall structures which may otherwise cast shadows, and the dynamically varying light source directions reduce glare which otherwise may be a problem. Advantageously, it is not needed to provide a structured light source. Advantageously, the system is less complex than that of US 2010/0149315 A1.

Optionally, the processor is arranged for stabilizing the region of interest across the series of images prior to applying the photometric stereo technique to the image data. Stabilizing refers decreasing or entirely avoiding variations in the spatial position of the region of interest in the series of images by suitably modifying said spatial position in each or multiple of the series of images. Accordingly, after said stabilizing, the region of interest is shown more steadily when successively viewing the series of images, i.e., as a sequence. It is noted that when viewing the series of images simultaneously instead of sequentially, e.g., in a side-by-side manner, such stabilizing is also referred to as image alignment or registration as the region of interest is more aligned or better registered across the series of images. It has been found that such stabilization results in a better estimate of the plurality of surface parameters. Advantageously, a better 3D surface profile of the region of interest is obtained.

Optionally, the system further comprises an inertial sensor for estimating movement of the imaging sensor during the acquiring of the series of images, and the processor is arranged for stabilizing the region of interest across the series of images based on sensor data received from the inertial sensor. Variations of the spatial position of the region of interest in the series of images are frequently due to movement of the imaging sensor. For example, if the imaging sensor is attached to a colposcope, a user such as a clinician operating the colposcope may inadvertently cause the colposcope to shake or otherwise move while acquiring the series of images. By including the inertial sensor, e.g., affixed to the imaging sensor or to a part of the system which moves with the imaging sensor, the movement of the imaging sensor during the acquiring of the series of images is estimated. Accordingly, the movement can be compensated in the series of images, thereby stabilizing the region of interest in the series of images. Advantageously, the inertial sensor can be used alternatively or additionally to image-based stabilization of the region of interest. Advantageously, a better 3D surface profile of the region of interest is obtained.

Optionally, the processor is arranged for using the 3D surface profile of the region of interest to enhance images acquired by the imaging sensor. It has been found that the 3D surface profile is well suited in enhancing images acquired by the image sensor, such as the series of images or subsequently acquired images.

Optionally, the processor is arranged for using the 3D surface profile of the region of interest to stabilize the region of interest in the images acquired by the imaging sensor. Having obtained the 3D surface profile, the 3D surface profile can be used to stabilize the region of interest in the images acquired by the imaging sensor. Advantageously, a user such as a clinician can better focus on the region of interest in the images since less or no effort is required to track the region of interest while viewing the series of images. Advantageously, a better stabilization is obtained when using 3D information, e.g., the 3D surface profile, instead of having to rely only on 2D information, e.g., the image data itself.

Also the processor is arranged for using the 3D surface profile of the region of interest to detect insufficiently illuminated areas of the region of interest in the images acquired by the imaging sensor. The processor thus infers from the 3D surface profile of the region of interest which areas of the region of interest are poorly illuminated in the images acquired by the imaging sensor. The processor is enabled to do so since the illumination of each area of the region of interest depends on the orientation and/or position of said areas, and in particular the orientation and/or position with respect to the plurality of light sources and the imaging sensor. The 3D surface profile of the region of interest is indicative of the orientation and/or position of each area of the region of interest.

Optionally, the processor is arranged for processing the images acquired by the imaging sensor to enhance a brightness and/or contrast of the insufficiently illuminated areas of the region of interest. By enhancing the brightness and/or contrast of the insufficiently illuminated areas of the region of interest, said areas of the region of interest are made visible or better visible in the images. Advantageously, a user such as a clinician is provided with images which better show the region of interest. Advantageously, areas which are difficult to illuminate using light sources can be synthetically illuminated by the system.

Optionally, the processor is arranged for instructing the lighting controller to increase the illuminating by the plurality of light sources in the insufficiently illuminated areas of the region of interest in the patient's interior. The insufficiently illuminated areas of the region of interest are thus better illuminated by the plurality of light sources, e.g., by an increased light output, a different subset of the plurality of light sources, etc. Advantageously, the user is provided with images which better show the region of interest.

Optionally, the system is arranged for maintaining a fixed physical relation between the plurality of light sources and the imaging sensor during the acquiring of the series of images. By establishing a fixed physical relation between the plurality of light sources and the imaging sensor during the acquiring of the series of images, the applying of the photometric stereo technique is facilitated since it is not needed anymore to otherwise compensate for a change in the physical relation during the acquiring of the series of images. Advantageously, a better 3D surface profile of the region of interest is obtained.

Optionally, the individual ones of the plurality of light sources are arranged on a ring-shaped structure, and the ring-shaped structure is affixed around the imaging sensor. A ring-shaped structure is particularly well suited for establishing dynamically varying light source directions since the imaging sensor will typically be oriented towards the region of interest, thereby providing the plurality of light sources with a wide range of light source directions with respect to the region of interest, e.g., substantially 360 degrees. A wide range of light source directions facilitates the applying of the photometric stereo technique. Advantageously, a better 3D surface profile of the region of interest is obtained.

Optionally, the processor is arranged for, when operating in a calibration mode, measuring the different light source directions based on detecting reflections in images acquired by the imaging sensor. Detecting the reflections in images acquired by the imaging sensor provides a convenient manner of making the different light source directions known to the system. Accordingly, if the lighting data comprises static data which indicates the light source directions provided by each of the different subsets of the plurality of light sources, said static data can be conveniently obtained in the calibration mode. Advantageously, it is not needed to otherwise manually measure the different light source directions in order to make the different light source directions known to the system.

Optionally, the system further comprises a scope being one of the group of: a colposcope, a laparoscope, an ophthalmoscope and a retinoscope, the scope comprising the plurality of light sources and the imaging sensor.

It will be appreciated by those skilled in the art that two or more of the above-mentioned embodiments, implementations, and/or aspects of the invention may be combined in any way deemed useful.

Modifications and variations of the workstation, the imaging apparatus, the method, and/or the computer program product, which correspond to the described modifications and variations of the system, can be carried out by a person skilled in the art on the basis of the present description.

A person skilled in the art will appreciate that the method may be applied to multi-dimensional image data, e.g. to two-dimensional (2D), three-dimensional (3D) or four-dimensional (4D) images. A dimension of the multi-dimensional image data may relate to time. For example, a 3D image may comprise a time-series of 2D images.

The invention is defined in the independent claims. Advantageous embodiments are defined in the dependent claims.

BRIEF DESCRIPTION OF THE DRAWINGS

These and other aspects of the invention are apparent from and will be elucidated with reference to the embodiments described hereinafter. In the drawings.

FIG. 4a shows a frontal view of a scope, the scope comprising a plurality of light sources and an imaging sensor, and the plurality of light sources being arranged on a ring-shaped structure which is affixed around the imaging sensor;

FIG. 4b shows a side view of the scope;

FIG. 5 shows an image acquired by the imaging sensor, the image showing a region of interest which is illuminated by individual ones of the plurality of light sources;

FIG. 6a shows a first image from a series of images, said image showing the region of interest being illuminated by a first one of different subsets of light sources;

FIGS. 6b, 6c and 6d show a second, third and fourth image showing the region of interest being illuminated by a second, third and fourth one of the different subsets of light sources, respectively.

DETAILED DESCRIPTION OF EMBODIMENTS

Figure 1:
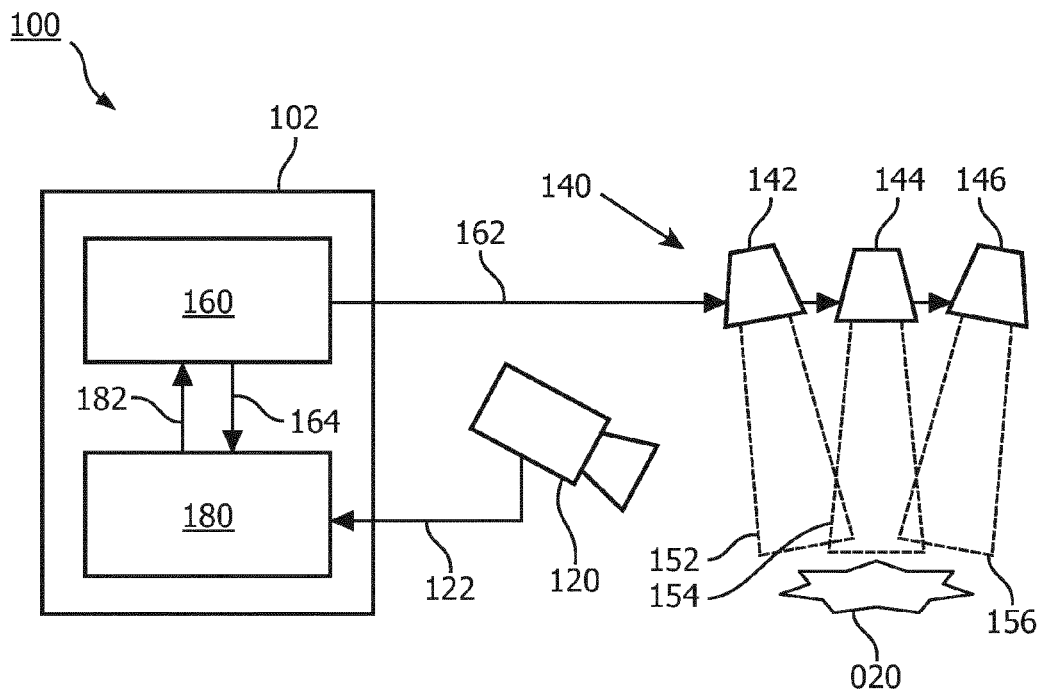
FIG. 1 shows a system for imaging a patient's interior.

FIG. 1 shows a system 100 for imaging a patient's interior. The system 100 comprises an imaging sensor 120 for acquiring, in the form of image data 122, a series of images of a region of interest 020 in the patient's interior. For illustration purposes, the region of interest 020 is shown schematically in FIG. 1 by means of a star-shaped region, without showing the patient's interior nor the patient itself.

It will be appreciated that during actual use of the system 100, the imaging sensor 120 will be positioned such that it is directed at a region of interest in the patient's interior, e.g., by being inserted into the patient's interior, directed at an opening in the patient's interior, etc. The system 100 further comprises a plurality of light sources 140 for illuminating the region of interest 020 in the patient's interior from different light source directions 152-156. By way of example, FIG. 1 shows the plurality of light sources 140 being comprised of a first light source 142 illuminating the region of interest 020 from a first light source direction 152, a second light source 144 illuminating the region of interest 020 from a second light source direction 154, and a third light source 146 illuminating the region of interest 020 from a third light source direction 156. The different light source directions 152-156 are different in that the principle light output direction of each of the plurality of light sources 140 differs, e.g., is represented by a different vector in 3D space. By way of example, FIG. 1 shows the first light source direction 152 to be oblique with respect to the surface of the region of interest 020, the second light source direction 154 to be orthogonal with respect to the surface, and the third light source direction 156 to be differently oblique with respect to the surface. Accordingly, the region of interest 020 is shown to be illuminated from three different directions.

The system 100 further comprises a light controller 160 for controlling individual ones 142-146 of the plurality of light sources 140 to illuminate the region of interest with different subsets 410-440 of the plurality of light sources when acquiring the series of images. For that purpose, the light controller 160 is shown to provide control data 162 to each of the plurality of the light sources 140, e.g., via wired or wireless signals. Accordingly, the light controller is enabled to establish dynamically varying light source directions while the imaging sensor 120 acquires the series of images. In particular, the light controller is enabled to establish a different light source direction for each or a subset of the series of images. The system 100 further comprises a processor 180 for obtaining lighting data 164 indicative of the dynamically varying light source directions. By way of example, FIG. 1 shows the processor 180 obtaining the lighting data 164 from the light controller 160. Accordingly, the lighting data 164 may comprise or may be comprised of the control data 162. However, this is not a limitation, in that the lighting data 164 may also take other forms and may be obtained in a different manner, i.e., not from the light controller 160. The processor 180 is further arranged for using the lighting data 164 to apply a photometric stereo technique to the image data 122 for estimating a plurality of surface parameters defining a surface of the region of interest 020 in the series of images. For that purpose, the processor 180 is shown to receive the image data 122 from the imaging sensor. Moreover, the processor 180 is arranged for, based on the surface parameters, establishing a 3D surface profile of the region of interest. Although not shown in FIG. 1, the processor 180 may output the 3D surface profile, e.g., to a display for display thereon, or to a storage medium for storage thereon. For example, the processor 180 may output the 3D surface profile in the form of a color based depth map to show the 3D surface profile to the user in an easy-to-interpret manner.

An operation of the system 100 may be briefly explained as follows. The light controller 160 controls individual ones 142-146 of the plurality of light sources 140 to illuminate the region of interest 020 with different subsets 410-440 of the plurality of light sources, thereby establishing dynamically varying light source directions. At an approximately same time, e.g., in synchronicity or simultaneously with the dynamically varying light source directions, the imaging sensor acquires the series of images of the region of interest 020 in the patient's interior, thereby providing image data 122 of the series of images. The processor 180 obtains lighting data 164 indicative of the dynamically varying light source directions. Moreover, the processor obtains the image data 122 from the imaging sensor 120. The processor 180 then uses the lighting data 164 to apply a photometric stereo technique to the image data 122 to estimate the plurality of surface parameters defining the surface of the region of interest 020 in the series of images. Furthermore, the processor uses the surface parameters to establishing a 3D surface profile of the region of interest 020.

It is noted that FIG. 1 further shows an optional aspect of the present invention, in that the processor 180 may provide instructions 182 to the light controller. This aspect of the present invention will be further discussed with reference to FIGS. 6a-6d.

Figures 2, 3:
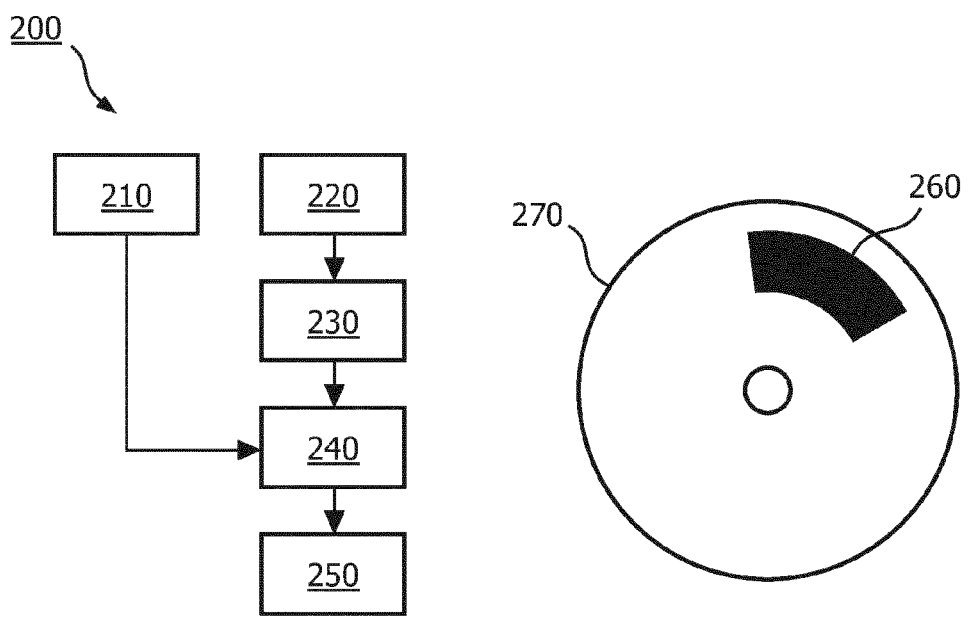
FIG. 2 shows a method for imaging the patient's interior.
FIG. 3 shows a computer program product for performing the method.

FIG. 2 shows a method 200 for imaging a patient's interior. The method 200 may correspond to an operation of the system 100. However, the method 200 may also be performed in separation of the system 100, e.g., using a different system or device.

The method 200 comprises, in a step titled "ACQUIRING SERIES OF IMAGES", acquiring 210, in the form of image data, a series of images of a region of interest in the patient's interior, the region of interest being illuminated in the patient's interior by a plurality of light sources from different light source directions. The method 200 further comprises, in a step titled "DYNAMICALLY VARYING LIGHT SOURCE DIRECTIONS", controlling 220 individual ones of the plurality of light sources to illuminate the region of interest with different subsets of the plurality of light sources when acquiring the series of images, thereby establishing dynamically varying light source directions during said acquiring. The method 200 further comprises, in a step titled "OBTAINING LIGHTING DATA", obtaining 230 lighting data indicative of the dynamic sequence of light source directions. Furthermore, the method 200 comprises, in a step titled "ESTIMATE SURFACE PARAMETERS", using the lighting data to apply 240 a photometric stereo technique to the image data for estimating a plurality of surface parameters defining a surface of the region of interest in the series of images. The method 200 further comprises, in a step titled "ESTABLISHING 3D SURFACE PROFILE", based on the surface parameters, establishing (250) a three-dimensional [3D] surface profile of the region of interest. It will be appreciated that the steps of the method 200 may be performed in any suitable order. In particular, the steps of acquiring 210 and controlling 220 may be performed at an approximately same time, e.g., synchronously or simultaneously. Another example is that the step of obtaining 230 may be performed before, during or after the steps of acquiring 210 and controlling 220.

FIG. 3 shows a computer program product 260 comprising instructions for causing a processor system to perform the method according to the present invention. The computer program product 260 may be comprised on a computer readable medium 270, for example as a series of machine readable physical marks and/or as a series of elements having different electrical, e.g., magnetic, or optical properties or values.

The system 100 and the method 200, and various optional aspects of the system 100 and the method 200, will be further explained with reference to FIGS. 4a-6d.

FIG. 4a shows a frontal view and FIG. 4b shows a side view of a scope 110 which may be used in the imaging of the patient's interior. As such, the scope 110 may be a colposcope, a laparoscope, an ophthalmoscope, a retinoscope or any other type of scope. The scope 110 is shown to comprise the imaging sensor 120. Although shown in FIGS. 4a and 4b as a relatively flat element, the imaging sensor 120 may in practice comprise optics such as one or more lenses and a photosensitive array such as a CCD or CMOS array. However, this is not a limitation in that the imaging sensor 120 may equally take any other suitable form. FIGS. 4a and 4b further show the scope being provided with a plurality of light sources 140 which are arranged on a ring-shaped structure 130 with said structure being affixed around the imaging sensor 120. Accordingly, a fixed physical relation may be maintained between the plurality of light sources 140 and the imaging sensor 120 during the acquiring of the series of images. FIG. 4a shows the plurality of light sources 140 head-on, i.e., facing a light-emitting end of the light sources. The ring-shaped structure 130 may be a circular carrier such as a printed circuit board (PCB), which may be encapsulated so as to allow entry into the patient's interior. The plurality of light sources 140 may be a plurality of Light Emitting Diodes (LEDs). Other examples of suitable light sources 140 include laser-based light sources, fibre-optics based light-sources, infrared (IR) light emitting light sources or any other transducers which generates a directional response at the imaging sensor 120. For example, the plurality of light sources 140 may be provided by an integrated LED array on chip, or may be constituted by a set of optical fibres which are expanded in a controlled way using a stent-like apparatus upon reaching a desired position within the patient's interior.

FIG. 4a further shows a subset 400 of the plurality of light sources 140 being activated. This is indicated by a star-shaped contour surrounding said light sources 140. Here, the subset 400 of light sources is constituted by two light sources, the two light sources being arranged opposite in the circular shape, i.e., a top one and a bottom one of the plurality of light sources 140 when viewed head-on. The others of the plurality of light sources 140 are not activated, being indicated by the star-shaped contour being absent. FIG. 4b further illustrates the different light source directions 150 established by the subset 400 of light sources. In this respect, it is noted that each of the plurality of light sources 140 in itself may be differently oriented so as to establish the different light source directions 150. For example, each of the plurality of light sources 140 may be oriented towards the region of interest 020, i.e., along the optical axis of the imaging sensor 120. However, it is noted that the different light source directions 150 are also established if the orientation of each of the plurality of light sources 140 is the same, e.g., forward facing. In this case, the different light source directions are already established due to the difference in position of each of the plurality of light sources 140 with respect to the region of interest 020, resulting in the region of interest 020 being illuminated from different light source directions 150.

Although not shown in FIGS. 4a and 4b, the plurality of light sources 140 may also be arranged on multiple concentric ring-shaped structures which are affixed around the imaging sensor 120. Moreover, instead of a ring-shaped structure, another geometric pattern may be used, such as a square array. The plurality of light sources 140 may further provide differently colored light, e.g., to yield color dependent diagnostic abilities in colposcopy. For that purpose, the plurality of light sources 140 may be constituted by different types of light sources. Alternatively, the light sources 140 may be adjustable in color characteristic.

It is noted that FIG. 4*b* further shows an inertial sensor 112 for estimating movement of the scope 110 and thus of the imaging sensor 120 affixed to the scope 110. This aspect of the present invention will be further discussed with reference to FIGS. 6*a*-6*d*.

It is further noted that, although not shown in FIGS. 4*a* and 4*b*, the plurality of light sources 140 may be adjustable in orientation, e.g., by means of the ring-shaped structure 130 being tiltable, shiftable, etc., with respect to the optical axis of the image sensor 120. Hence, by adjusting the orientation of the ring-shaped structure 130, the orientation of all of the plurality of light sources 140 may be adjusted. Any such adjustment may be performed before or after acquiring the series of images, thereby enabling maintaining a fixed physical relation with respect to the imaging sensor 120 during the acquiring of the series of images. A purpose of said tiltability or shiftability may be avoid glare from a specific portion of the surface, with the presence of such glare being determined by the system 100 from images acquired by the imaging sensor 120. Another purpose of said tiltability or shiftability may be that on having determined the 3D surface profile of the region of interest, a user may better maneuver the scope 110 or similar part of the system 100 in constricted space within the patient's interior to obtain a better view of the region of interest with the imaging sensor 120.

FIG. 5 shows an image 300 acquired by the imaging sensor, the image showing a region of interest 020 which is illuminated by individual ones of the plurality of light sources 140. For illustration purposes, the region of interest 020 shown in the image 300 is a portion of the exterior of an apple. It is noted, however, that during actual use of the system 100, the region of interest 020 typically constitutes a region of interest within a patient's interior, e.g., the cervix or part thereof. The image 300 shows the region of interest being illuminated by the plurality of light sources 140 as shown in FIG. 4*a*. Hence, the subset 300 of two opposite light sources is used in illuminating the region of interest. As a result of the surface of the apple's exterior being shiny, specular reflections occur which result in bright regions being visible in the image 162. It is noted that such types of reflections may be used deliberately during a calibration procedure, namely to measure the different light source directions 150. In particular, a mirrored object such as a sphere or a flat mirror may be placed in front of the imaging sensor 120 at a specified distance, and the reflection of each of the plurality sources of light may be recorded by the imaging sensor 120, e.g., by sequentially activating each of the plurality of light sources 140 and acquiring a corresponding image. From said images, a light source direction of each of the plurality of light sources 140 may be calculated, with the result serving as a static part of the lighting data 164.

FIGS. 6*a*-6*d* shows a series of images 310-340 which has been acquired by the imaging sensor 120 while the light controller 160 controls individual ones of the plurality of light sources 140 to illuminate the region of interest with different subsets 410-440 of the plurality of light sources when acquiring the series of images, thereby establishing dynamically varying light source directions during said acquiring. Consequently, FIG. 6*a* shows a first image 310 and a first subset of light sources 410, FIG. 6*b* shows a second image 320 and a second subset of light sources 420, FIG. 6*c* shows a third image 330 and a third subset 430 of light sources, and FIG. 6*d* shows a fourth image 440 and a fourth subset of light sources 340. It can be see that the illumination by the different subsets 410-440 of light sources causes the appearance of the region of interest to vary across the series of images 310-340, i.e., resulting in a first 021, second 022, third 023 and fourth appearance 024.

Based on the dynamically changing appearance of the region of interest across the series of images 310-340, the processor 180 may establish a 3D surface profile of the region of interest 020-024 as follows. Firstly, the processor 180 may obtain data from the light controller 160 which indicates which subset of light sources are used during the acquiring of each of the series of images 310-340. The processor 180 may already be provided with a light source direction of each of the plurality of light sources 140, e.g., during a calibration procedure. Accordingly, the processor 180 may be provided with lighting data 164 which indicates from which light source direction(s) the region of interest 020-024 is illuminated in each of the series of images 310-340. The processor 180 may then use the lighting data 164 and the image data 122 of the series of images 310-340 in a photometric stereo technique. Such techniques are known per se. For example, a photometric stereo technique may be applied as described in "Photometric method for determining surface orientation from multiple images", Woodham R. J., Optical Engineering, January/February 1980, Vol. 19, No. 1, pp. 139-144. The application of such a photometric stereo technique in the context of the present invention is based on the following recognitions. Unlike the surface of the apple's exterior, the actual region of interest 020-024 in a patient's interior typically provides a diffusely reflective surface can be modeled by a Lambertian reflectance model. In such Lambertian reflectance, the apparent brightness of such a surface to an observer is the same, i.e., isotropic, regardless of the observer's angle of view. Accordingly, a surface providing Lambertian reflectance has the same apparent brightness when viewed from any angle, because the emitted total light and the projected area are both reduced by the cosine of the viewing angle. Under this assumption, the observed intensities by the imaging sensor 120, i.e., as obtained from an image acquired of the region of interest, can be expressed as follows:

$$I = (\rho/\pi) \cdot b \cdot c \cdot (n \cdot S)$$

Here, the term I is representation of the observed intensities of the region of interest, the term n is a representation of the surface normals across the region of interest, which are independent of the lighting and rather determined by the shape of the surface of the region of interest, and the term S is a representation of the light source direction(s). The term I may be provided by the image data of an acquired image. The term S may be provided by the lighting data indicating the light source direction(s) used in illuminating the region of interest in the acquired image. Furthermore, the term b is the light source brightness, the term $\rho$ is the surface albedo, and c is an optical system constant. It is further noted that (n·S) is the dot product (cosine) of the surface normal n and the light source direction S since the angle of the light falling on a Lambertian-modelled surface is the only factor which changes the observed intensity of said surface in the Lambertian reflectance model.

The processor 180 may estimate the plurality of surface parameters defining the surface of the region of interest in the series of images 310-340 by solving for the term n in the above equation, thereby obtaining surface normals of the region of interest. In particular, the processor 180 may make use of multiple acquired images, i.e., multiple ones of the series of images 310-340. For example, the processor 180 may solve for the term n by solving the following normalized 3×1 matrix equation:

$$\begin{bmatrix} I_1 \\ I_2 \\ I_3 \end{bmatrix} = \begin{bmatrix} s_1^T \\ s_2^T \\ s_3^T \end{bmatrix} n$$

namely by calculating the term n as:

$$n = S^{-1} I$$

Here, terms $I_1$, $I_2$ and $I_3$ are matrix representation of the intensities of respectively a first acquired image, a second acquired image and a third acquired image, together yielding a matrix representation of the term I, whereas the terms $S_1$, $S_2$ and $S_3$ are matrix representation of the light source direction(s) used in illuminating the region of interest in each acquired image, together yielding a matrix representation of the term S.

The processor 180 may also make use of more than three acquired images in which the region of interest is illuminated from different light source directions:

$$\begin{bmatrix} I_1 \\ I_2 \\ I_N \end{bmatrix} = \begin{bmatrix} s_1^T \\ s_2^T \\ s_N^T \end{bmatrix} n$$

In this case, however, the term S is not directly invertible anymore since the matrix S is no longer square. Therefore, the solution of the above equation may be obtained by first obtaining a square matrix, inverting it and carrying out the above computation of the normal n, namely by calculating the term n as follows:

$$n = (S^T S)^{-1} S^T I$$

It is noted that in case singularity arise during the inverting of the square matrix $S^T S$, this may be dealt with by the known technique of computing the SVD of the matrix, dropping the near-zero singular values, reducing the rank of the matrix after this, and inverting the diagonal and multiplying in the singular vectors to obtain a pseudo inverse.

The application of such a photometric stereo technique in the context of the present invention is further based on the following recognitions. The inventors have recognized that, in general, problems may arise in photometric stereo techniques due to shadows occurring on the surface of a region of interest which may not be properly accounted for in the photometric stereo technique. Moreover, problems may also arise due to the surface of the region of interest being specularly reflective instead of, or in addition to, being diffusely reflective. However, by the system 100 establishing dynamically varying light source directions during the acquiring of the series of images, the problems due to specularly reflective surface are reduced or entirely avoided. Moreover, the system 100 being used for imaging a region of interest in a patient's interior, with such regions being typically convex and not having tall structures, the occurrence of shadows on the surface of the region of interest is reduced or entirely avoided. For example, the inventors have recognized that the system 100 may be well applied to a cervical region which is examined as part of a colposcopy, as well as a wide variety of other regions of interest within a patient's interior.

Having estimated the surface normals of the surface of the region of interest, the processor 180 may establish a 3D surface profile of the region of interest based on the surface normals, e.g., by constructing a polygonal model of the surface which fits the surface normals. In this respect, it is noted that instead of estimating the surface normals of the surface of the region of interest, other surface parameters may be equally estimated and used in establishing the 3D surface profile. For example, tangent vectors may be estimated.

In general, the processor 180 may be arranged for stabilizing the region of interest 020-024 in the series of images 310-340 prior to applying the photometric stereo technique to the image data 122. A reason for this may be that successive ones of the series of images, as obtained by the system 100 to construct the above two equations, are typically obtained at finite, non-zero time intervals, i.e., as determined based on the frame rate at which the images are acquired. During such time intervals, the region of interest 020-024 and/or the imaging sensor 120 may have moved. In such a case, stabilizing the region of interest 020-024 across the series of images 310-340 improves the accuracy of the photometric stereo technique. For that purpose, the processor 180 may make use of an image stabilization technique as is known per se from the fields of image and/or video processing. Accordingly, the processor 180 may detect a position of the region of interest 020-024 in each of the series of images 310-340, e.g., using a region of interest detection technique, and then apply a filter to the detected positions of the region of interest to dampen out or entirely eliminate variations of the position of the region of interest 020-024 across the series of images 310-340. As a result, a stabilized series of images may be obtained, which may then be used in the photometric stereo technique. Another example is that an inertial sensor 112 may be used to estimate movement of the imaging sensor 120 during the acquiring of the series of images 310-340. For example, the inertial sensor 112 may be provided on a scope 110 to which the imaging sensor 120 is affixed, as previously illustrated in FIG. 4b. The processor 180 may be arranged for stabilizing the region of interest 020-024 in the series of images based on sensor data received from the inertial sensor 112. Again, a stabilized series of images may be obtained, which may then be used in the photometric stereo technique. Yet another example is that the movement of the region of interest 020-024 may be estimated by computing blur in one or more images in which the region of interest is illuminated by a given subset of light sources so as to estimate the movement of the region of interest in a direction orthogonal to the light source direction(s) of the given subset of light sources.

Furthermore, the processor 180 may be arranged for using the 3D surface profile of the region of interest 020-024 to enhance images acquired by the imaging sensor 120. In particular, the processor 180 may enhance the images acquired by the imaging sensor 120 to improve a visibility of the region of interest. A first example is that the processor 180 may be arranged for using the 3D surface profile of the region of interest to stabilize the region of interest 020-024 in the images acquired by the imaging sensor 120. For that purpose, the processor 180 may fit the 3D surface profile of the region of interest to each of the acquired images to detect its position. A filter may then be applied to the detected positions of the region of interest to dampen out or entirely eliminate variations of the position of the region of interest 020-024 across the acquired images. Accordingly, a viewer of such images may be provided with a more stable display of the region of interest 020-024, i.e., with less or no variations in the position of the region of interest across the images.

A further example is that the processor 180 may be arranged for using the 3D surface profile of the region of interest to detect insufficiently illuminated areas of the region of interest 020-024 in the images acquired by the imaging sensor 120. For that purpose, the processor 180 may use the photometric stereo technique to determine the surface albedo in addition to the surface normal. Here, a low surface albedo may indicate an insufficient illumination of the respective area of the region of interest. Additionally or alternatively, the processor 180 may use the 3D surface profile to determine the distance of areas of the region of interest 020-024 to the imaging sensor 120, and correlate said distance to a brightness of the region of interest in the acquired images to determine if the area is insufficiently illuminated. For example, if an area of the region of interest is distanced from the imaging sensor and has a low brightness, this may indicate that the area is insufficiently illuminated.

The processor 180 may be further arranged for processing the images acquired by the imaging sensor 120 to enhance a brightness and/or contrast of the insufficiently illuminated areas of the region of interest 020-024. Accordingly, the processor 180 may increase a value of the luminance component of the pixels in said areas in the acquired images, e.g., by adding an offset to the luminance component, multiplying the luminance component with a gain value, applying a transfer function, etc. Additionally or alternatively, the processor 180 may be arranged for instructing the lighting controller 160 to increase the illuminating by the plurality of light sources 140 in the insufficiently illuminated areas of the region of interest 020-024 in the patient's interior. Accordingly, the lighting controller 160 may increase the brightness of one or more of the plurality of light sources 140, use additional or different ones of the plurality of light sources in the illuminating, etc.

Figure 7A:
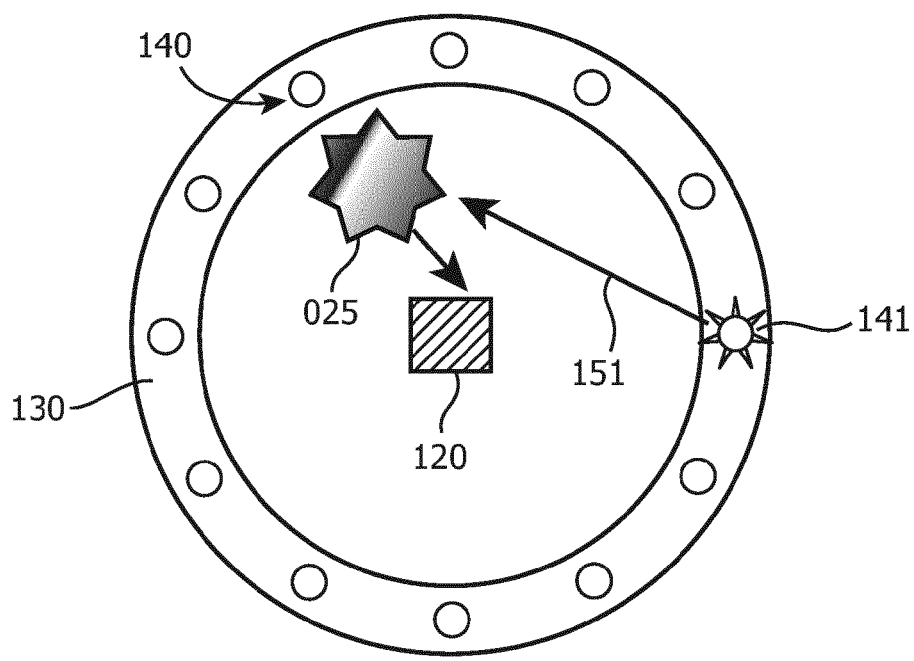
FIGS. 7a and 7b illustrate the system improving the illumination of previously insufficiently illuminated areas of the region of interest.
Figure 7B:
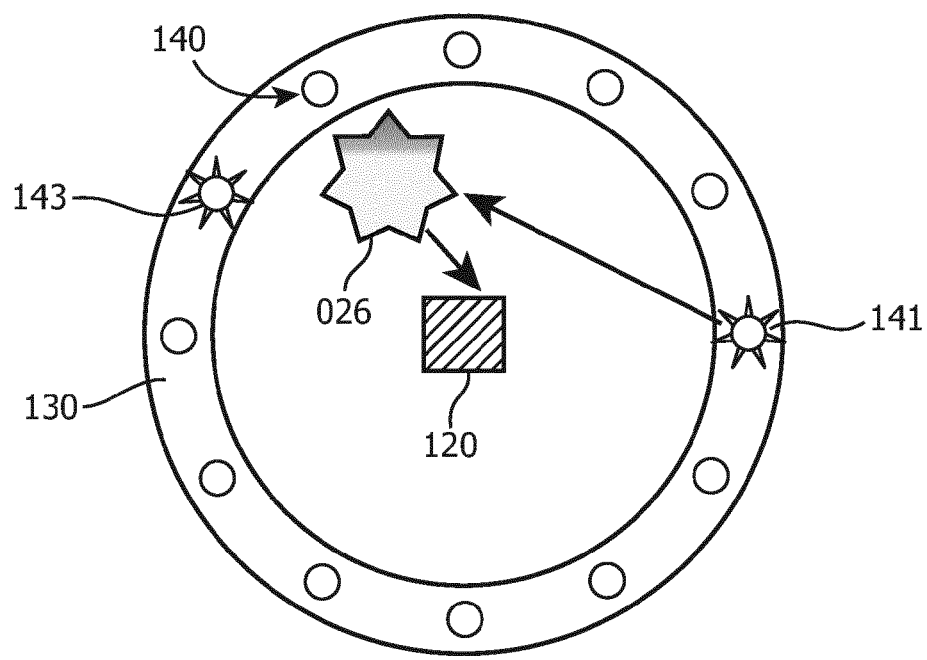

FIGS. 7a and 7b illustrate this principle. Here, the ring-shaped structure 130 has been enlarged for illustration purposes to show the region of interest 025-026 being illuminated from different light source directions by respective ones of the surrounding plurality of light sources 140. In particular, FIG. 7a shows the region of interest 025 being illuminated by a first light source 141 which illuminates the region of interest 025 from a southeast light source direction 151. As a result, northwestern areas of the region of interest 025 are poorly illuminated. The processor 180 may instruct the light controller 160 to additionally illuminate the region of interest 025 with a further light source 143 to increase the illuminating of the region of interest 025. FIG. 7b shows a result of this, in that the region of interest 026 is better illuminated, namely additionally from an eastern light source direction 153. As a result, the region of interest 026 is better illuminated. Additionally or alternatively, when the plurality of light sources 140 are adjustable in orientation, e.g., by means of the earlier mentioned ring-shaped structure 130 being tiltable, shiftable or otherwise adjustable, said adjustability may be used to increase the illuminating of the region of interest. For example, the plurality of light sources 140 may be tilted or shifted towards a steeply sloping part of the region of interest with is poorly illuminated. Such steeply sloping part may be determined by the system from the 3D surface profile of the region of interest.

It will be appreciated that the 3D surface profile of the region of interest may be used in various ways, such as in image enhancement, medical diagnosis, etc. For example, if the 3D surface profile has a certain 'bumpy' or 'mosaic-like' pattern, this may be indicative of lesions. Such a pattern is more easily discernible in a 3D surface profile of the region of interest than from a 2D view of the region of interest. Another example is that a focal range of the imaging sensor 120 may be adjusted based on the 3D surface profile. For example, the system may obtain a uniformly sharp image of the region of interest by sequentially passing through the depth range of the region of interest and acquiring images thereof, with the processor then combining said images into a uniformly sharp image of the region of interest.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. System for imaging a patient's interior, the system comprising an imaging sensor for acquiring, in the form of image data, a series of images of a region of interest in the patient's interior, the system further comprising:
    a plurality of light sources for illuminating the region of interest in the patient's interior from different light source directions:
    a light controller for controlling individual ones of the plurality of light sources to illuminate the region of interest with different subsets of the plurality of light sources when acquiring the series of images, thereby establishing dynamically varying light source directions during said acquiring; and
    a processor for i) obtaining lighting data indicative of the dynamically varying light source directions, ii) using the lighting data to apply a photometric stereo technique to the image data for estimating a plurality of surface parameters defining a surface of the region of interest in the series of images, iii) based on the surface parameters, establishing a three-dimensional [3D] surface profile of the region of interest, and iv) detecting insufficiently illuminated areas of the region of interest in the images acquired by the imaging sensor, using the 3D surface profile of the region of interest.

2. System according to claim 1, wherein the processor 1 is arranged for stabilizing the region of interest across the series of images prior to applying the photometric stereo technique to the image data.

3. System according to claim 2, further comprising an inertial sensor for estimating movement of the imaging sensor during the acquiring of the series of images, and wherein the processor is arranged for stabilizing the region of interest across the series of images based on sensor data received from the inertial sensor.

4. System according to claim 1, wherein the processor is arranged for using the 3D surface profile of the region of interest to enhance images acquired by the imaging sensor.

5. System according to claim 4, wherein the processor is arranged for using the 3D surface profile of the region of interest to stabilize the region of interest in the images acquired by the imaging sensor.

6. System according to claim 1, wherein the processor is arranged for processing the images acquired by the imaging sensor to enhance a brightness and/or contrast of the insufficiently illuminated areas of the region of interest.

7. System according to claim 1, wherein the processor is arranged for instructing the lighting controller to increase the illuminating by the plurality of light sources in the insufficiently illuminated areas of the region of interest in the patient's interior.

8. System according to claim 1, wherein the system is arranged for maintaining a fixed physical relation between the plurality of light sources and the imaging sensor during the acquiring of the series of images.

9. System according to claim 8, wherein the individual ones of the plurality of light sources are arranged on a ring-shaped structure, and wherein the ring-shaped structure is affixed around the imaging sensor.

10. System according to claim 8, wherein the processor is arranged for, when operating in a calibration mode, measuring the different light source directions based on detecting reflections in images acquired by the imaging sensor.

11. System according to claim 8, further comprising a scope being one of the group of: a colposcope, a laparoscope, an ophthalmoscope, and a retinoscope, the scope comprising the plurality of light sources.

12. Workstation or imaging system comprising the light controller and the processor of the system according to claim 1.

13. A method for imaging a patient's interior, the method comprising acquiring, in the form of image data, a series of images of a region of interest in the patient's interior, the region of interest being illuminated in the patient's interior by a plurality of light sources from different light source directions, the method further comprising:
    controlling individual ones of the plurality of light sources to illuminate the region of interest with different subsets of the plurality of light sources when acquiring the series of images, thereby establishing dynamically varying light source directions during said acquiring;
    obtaining lighting data indicative of the dynamic sequence of light source directions;
    using the lighting data to apply a photometric stereo technique to the image data for estimating a plurality of surface parameters defining a surface of the region of interest in the series of images;
    based on the surface parameters, establishing a three-dimensional [3D] surface profile of the region of interest; and
    detecting insufficiently illuminated areas of the region of interest in the images acquired by the imaging sensor, using the 3D surface profile of the region of interest.

14. A computer program product stored in a computer readable storage medium comprising instructions for causing a processor system to perform the method according to claim 13.

* * * * *